United States Patent
Herman et al.

(10) Patent No.: US 7,655,444 B2
(45) Date of Patent: Feb. 2, 2010

(54) METHOD OF PREDICTING THE CLINICAL RESPONSE TO CHEMOTHERAPEUTIC TREATMENT WITH ALKYLATING AGENTS

(75) Inventors: James G. Herman, Timontown, MD (US); Stephen B. Baylin, Baltimore, MD (US); Manel Esteller, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 46 days.

(21) Appl. No.: 10/870,577

(22) Filed: Jun. 16, 2004

(65) Prior Publication Data

US 2004/0265887 A1 Dec. 30, 2004

Related U.S. Application Data

(63) Continuation of application No. 09/969,131, filed on Oct. 1, 2001, now Pat. No. 6,773,897.

(60) Provisional application No. 60/236,760, filed on Sep. 29, 2000.

(51) Int. Cl.
  *C12P 19/34* (2006.01)
  *C12Q 1/68* (2006.01)
  *C07H 21/02* (2006.01)
  *C07H 21/04* (2006.01)
(52) U.S. Cl. .......................... 435/91.2; 435/6; 536/24.3; 536/24.33; 536/23.1; 536/24.1
(58) Field of Classification Search .................. 435/7.1, 435/23, 24, 975
  See application file for complete search history.

(56) References Cited

U.S. PATENT DOCUMENTS

| 5,407,804 | A | * | 4/1995 | Yarosh | 435/7.4 |
| 5,817,514 | A | * | 10/1998 | Li et al. | 435/338 |
| 6,773,897 | B2 | * | 8/2004 | Herman et al. | 435/15 |

FOREIGN PATENT DOCUMENTS

| WO | WO 93/24837 A1 | 12/1993 |
| WO | WO 00/05419 A1 | 2/2000 |
| WO | WO 00/51369 A1 | 8/2000 |
| WO | WO 02/068694 A1 | 9/2002 |

OTHER PUBLICATIONS

Herman et al, Proc. Natl. Acad. Sci. USA, vol. 93, pp. 9821-9826, Sep. 1996.*
Woodcock et al, J. Biological Chemistry, vol. 272, No. 12, pp. 7810-7816, Mar. 21, 1997.*
Lenz G et al 'Promoter methylation and expression of DNA repair genes hMLH1 and MGMT in acute myeloid leukemia.' Ann Hematol. Oct. 2004;83(10):628-33.*
Costello JF et al 'Aberrant CpG-island methylation has non-random and tumour-type-specific patterns.' Nat Genet. Feb. 2000;24(2):132-8.*
Costello JF et al 'Graded methylation in the promoter and body of the O6-methylguanine DNA methyltransferase (MGMT) gene correlates with MGMT expression in human glioma cells.' J Biol Chem. Jun. 24, 1994;269(25):17228-37.*
Rietschel P. et al 'Phase II Study of Extended-Dose Temozolomide in Patients With Melanoma' J Clinical Oncology )2008) vol. 26, No. 14, pp. 2299-2304.*
Sekiguchi M. et al, J Cancer Res Clin Oncol (1996) 122:199-206.*
Brabender J. et al, Clinical Cancer Research (2003) vol. 9, p. 223-227.*
Juppner H, Bone (1995) vol. 17, No. 2, Supplement, pp. 39S-42S.*
Bearzatto et al., "Epigenetic Regulation of the *MGMT* and *hMSH6* DNA Repair Genes in Cells Resistant to Methylating Agents", *Cancer Research*, 60:3262-3270 (2000).
Esteller et al., "Inactivation of the DNA Repair Gene $0^6$-Methylguanine-DNA Methyltransferase by Promoter Hypermethylation is a Common Event in Primary Human Neoplasia", *Cancer Research*, 59:793-797 (1999).
Esteller et al., "Inactivation of the DNA-Repair Gene *MGMT* and the Clinical Response of Gliomas to Alkylating Agents", *The New England Journal of Medicine*, 343(19):1350-1654 (2000).
Esteller et al., "Promoter Hypermethylation of the DNA Repair Gene MGMT Predicts Survival and Response to Regimens Containing the Alkylating Agent Cyclophosphamide in B-Cell Diffuse Large Cell Lymphoma", *Proceedings of the American Association for Cancer Research*, 42:347 (2001).
Herfarth et al., "A Specific CpG Methylation Pattern of the *MGMT* Promoter Region Associated with Reduced MGMT Expression in Primary Colorectal Cancers", *Molecular Carcinogenesis*, 24:90-98 (1999).
Mineura et al., "Human Brain Tumor $0^6$-Methylguanine-DNA Methyltransferase mRNA and Its Significance as an Indicator of Selective Chloroethylnitrosourea Chemotherapy", *Int. J. Cancer (Pred. Oncol.)*, 69:420-425 (1996).

* cited by examiner

*Primary Examiner*—Stephen Kapushoc
(74) *Attorney, Agent, or Firm*—DLA Piper LLP (US)

(57) ABSTRACT

The present invention provides methods relating to chemotherapeutic treatment of a cell proliferative disorder. In particular, a method is provided for predicting the clinical response to certain types of chemotherapeutic agents. Alkylating agents, used for the treatment of certain types of tumors including tumors of the nervous system and lymph system, are efficacious agents when the damage they do to tumor cell DNA is not repaired by cellular DNA repair mechanisms. The present invention provides a method for determining the activity of a gene encoding a DNA repair enzyme, thus providing a prediction of the clinical response to alkylating agents.

7 Claims, 3 Drawing Sheets

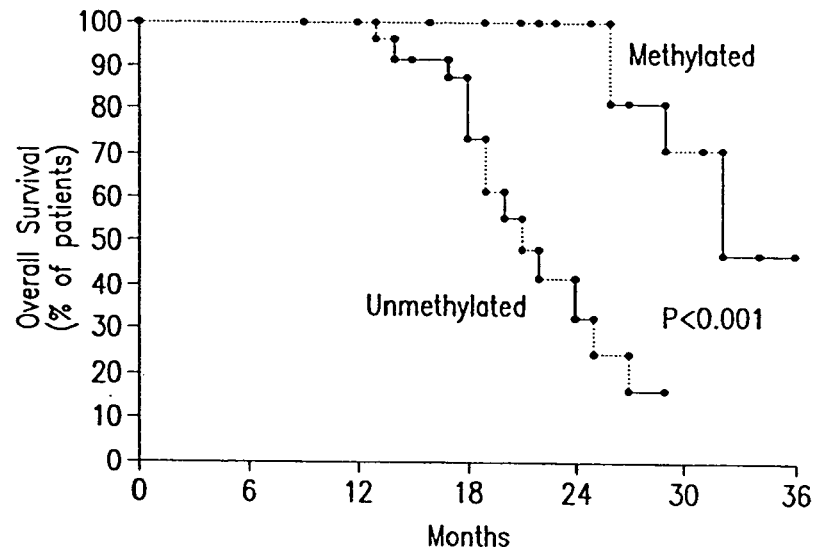
FIG. IA
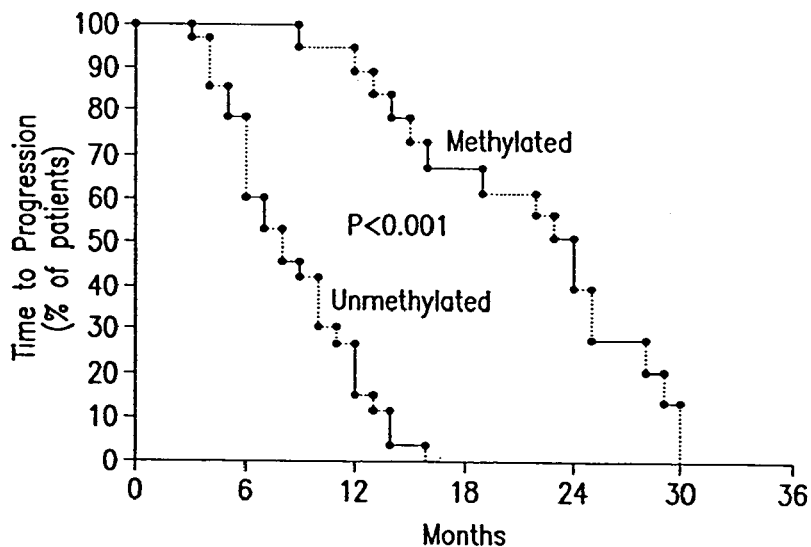
FIG. IB

SEQUENCE LISTING

```
<160> NUMBER OF SEQ ID NOS: 4

<210> SEQ ID NO 1
<211> LENGTH: 29
<212> TYPE: DNA
<213> ORGANISM: Artificial sequence
<220> FEATURE:
<223> OTHER INFORMATION: Forward primer

<400> SEQUENCE: 1
tttgtgtttt gatgtttgta ggtttttgt                                   29

<210> SEQ ID NO 2
<211> LENGTH: 28
<212> TYPE: DNA
<213> ORGANISM: Artificial sequence
<220> FEATURE:
<223> OTHER INFORMATION: Reverse primer

<400> SEQUENCE: 2
aactccacac tcttccaaaa acaaaaca                                    28

<210> SEQ ID NO 3
<211> LENGTH: 23
<212> TYPE: DNA
<213> ORGANISM: Artificial sequence
<220> FEATURE:
<223> OTHER INFORMATION: Forward primer

<400> SEQUENCE: 3
tttcgacgtt cgtaggtttt cgc                                         23

<210> SEQ ID NO 4
<211> LENGTH: 22
<212> TYPE: DNA
<213> ORGANISM: Artificial sequence
<220> FEATURE:
<223> OTHER INFORMATION: Reverse primer
```

```
<400> SEQUENCE: 4
gcactcttcc gaaaacgaaa cg                                          22
```

METHOD OF PREDICTING THE CLINICAL RESPONSE TO CHEMOTHERAPEUTIC TREATMENT WITH ALKYLATING AGENTS

CROSS REFERENCE TO RELATED APPLICATIONS

This application is a continuation of U.S. application Ser. No. 09/969,131 filed Oct. 1, 2001, now U.S. Pat. No. 6,773,897; which claims the benefit under 35 USC § 119(e) to U.S. Application Ser. No. 60/236,760 filed Sep. 29, 2000. The disclosure of each of the prior applications is considered part of and is incorporated by reference in the disclosure of this application.

FIELD OF INVENTION

The invention relates to the field of chemotherapeutic treatment and particularly to a method of predicting the clinical response to chemotherapeutic treatment with alkylating agents for the treatment of certain tumor types.

BACKGROUND OF THE INVENTION

Systemic chemotherapy is the primary treatment available for certain types of tumors and malignant diseases. Curative chemotherapeutic regimens and palliative chemotherapeutic regimens have been developed for many tumor types, often resulting in improved survival. Chemotherapy, whether given with curative or palliative intent, usually requires multiple cycles of treatment. Every chemotherapeutic regimen administered in adequate doses will have some deleterious side effect on normal host tissues.

Chemotherapeutic efficacy, the ability of chemotherapy to eradicate tumor cells without causing lethal host toxicity, depends of drug selectivity. The basis for anticancer drug selectivity is not completely understood. One class of anticancer drugs, alkylating agents, cause cell death by binding to DNA which structurally distorts the DNA helical structure preventing DNA transcription and translation. In normal cells, the damaging action of alkylating agents can be repaired by cellular DNA repair enzymes, in particular $O^6$-methylguanine-DNA methyltransferase (MGMT). The level of MGMT varies in tumor cells, even among tumors of the same type. The gene encoding MGMT is not commonly mutated or deleted. Rather, low levels of MGMT in tumor cells is due to an epigenetic modification; the MGMT gene is methylated preventing expression of MGMT.

Methylation has been shown by several lines of evidence to play a role in gene activity, cell differentiation, tumorigenesis, X-chromosome inactivation, genomic imprinting and other major biological processes. In eukaryotic cells, methylation of cytosine residues that are immediately 5' to a guanosine, occurs predominantly in cytosine-guanine (CG) poor regions. In contrast, CpG islands remain unmethylated in normal cells, except during X-chromosome inactivation and parental specific imprinting where methylation of 5' regulatory regions can lead to transcriptional repression. Expression of a tumor suppressor gene can also be abolished by de novo DNA methylation of a normally unmethylated CpG.

Hypermethylation of genes encoding DNA repair enzymes can serve as markers for predicting the clinical response to certain cancer treatments. Certain chemotherapeutic agents inhibit cellular proliferation by cross-linking DNA, resulting in cell death. Treatment efforts with such agents can be thwarted because DNA repair enzymes remove the cross-linked structures. In view of the deleterious side effects of most chemotherapeutic drugs, and the ineffectiveness of certain drugs for various treatments, it is desirable to predict the clinical response to treatment with chemotherapeutic agents. The present invention satisfies that need and others.

SUMMARY OF THE INVENTION

The present invention is based on the finding that the methylation state of a gene encoding a DNA repair enzyme is predictive of the clinical response to treatment with certain chemotherapeutic agents. Hypermethylation of the DNA repair enzyme $O^6$-methylguanine-DNA methyltransferase (MGMT) results in low levels of MGMT. Tumor cells treated with chemotherapeutic agents that cause damage to DNA do not survive because the MGMT is not available to repair the damage.

In one embodiment of the invention, there is provided a method of predicting a clinical response to treatment with a chemotherapeutic agent of a subject in need of treatment. The method includes determining the state of methylation of a nucleic acid isolated encoding a DNA repair enzyme from the subject. The repair enzyme impedes an activity of the chemotherapeutic agent. The state of methylation of the nucleic acid isolated from the subject in need of treatment with the state of methylation of a nucleic acid encoding the same enzyme from a subject not in need of treatment. A difference in the state of methylation is predictive of the clinical response to treatment with a therapeutic agent.

In another embodiment of the invention, there is provided a method of treating a cellular proliferative disorder with an alkylating chemotherapeutic agent in a subject that includes predicting a clinical response to treatment by determining the state of methylation of a nucleic acid encoding a DNA repair enzyme isolated from the subject. The enzyme impedes an activity of the chemotherapeutic agent. The state of methylation of the nucleic acid of the subject compared with the state of methylation of the nucleic acid from a subject not in need of treatment is indicative of the level of enzyme and the response to treatment.

In yet another embodiment of the invention there is provided a kit for predicting the response to chemotherapeutic treatment of a cellular proliferative disorder in a subject. The kit contains a reagent that modifies unmethylated cytosine nucleotides and at least one primer pair including sense primer and at least one antisense for amplification of CpG-containing nucleic acid in the regulatory region of $O^6$-methylguanine-DNA methyltransferase. The primers can distinguish between modified methylated and non-methylated nucleic acid.

BRIEF DESCRIPTION OF FIGURES

FIG. 1A shows the overall survival among subjects with gliomas treated with carmustine, according to the methylation status of the MGMT promoter.

FIG. 1B shows the time to the progression of disease, according to the methylation status of the MGMT promoter. Both overall survival and the time to the progression of disease were significantly greater in the group of subjects with methylation of the MGMT promoter than in the group without methylation. The association was independent of the type of tumor, the subject's age, and the Karnofsky score for performance status.

FIG. 2 shows an analysis of MGMT promoter hypermethylation in B-Diffuse large cell lymphomas treated with cyclophosphamide and its impact in survival.

FIG. 3 shows an analysis of the independence of MGMT promoter methylation and IPI (International Prognostic Index) in B-Diffuse large cell lymphomas on survival. Subjects classified as Low (L), Low-intermediate (LI), High-intermediate (HI) or High (H) risk according to the IPI, and for visual clarity, subjects>L were combined.

DETAILED DESCRIPTION OF THE INVENTION

Figure 2A:
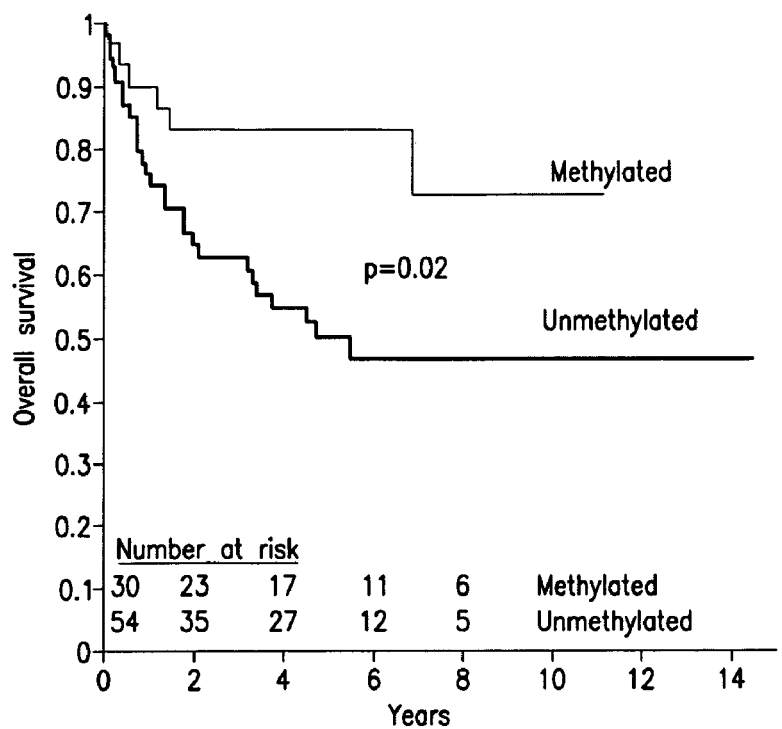
FIG. 2A shows overall survival as a function of MGMT methylation status.

The invention is based on the discovery that the methylation state of nucleic acids of certain genes, particularly regulatory sequences, is predictive of clinical response to treatment with chemotherapeutic agents. More particularly, the hypermethylation of certain nucleotides localized in CpG islands has been shown to affect the expression of genes associated with the CpG islands; typically such hypermethylated genes have reduced or abolished expression, primarily due to down-regulated transcription. Hypermethylation of the regulatory region of a DNA repair enzyme allows one to predict a clinical response to treatment with a chemotherapeutic agent. Using a recently developed polymerase chain reaction (PCR)-based technique called methylated specific PCR (MSP) tumor cells with hypermethylated MGMT can be identified, thereby allowing one to predict the response of the tumor cells to treatment with a therapeutic agent. These methods are described in U.S. Pat. No. 5,786,146, issued Jul. 28, 1998; U.S. Pat. No. 6,017,704, issued Jan. 25, 2000; U.S. Pat. No. 6,200,756, issued Mar. 13, 2001; and U.S. Pat. No. 6,265,171, issued Jul. 24, 2001; the entire contents of each of which is incorporated herein by reference.

DNA repair enzymes play a major role in mutagenesis, carcinogenesis and resistance to genotoxic agents. DNA repair enzymes recognize and correct damage to DNA. The rate of mutation reflects a balance between the number of damaging events occurring in DNA and the number that have been corrected. Damage to DNA consists of any change that is deviation from the usual double helical structure of DNA. Two general classes of DNA damage are observed. Single base changes affect the sequence of the DNA strand but not the structure of the strand. Structural distortions provide a physical impediment to replication or transcription. For example, ultraviolet irradiation results in unusual thymine dimers. Alkylating agents results in additional alkyl groups attached to bases.

Alkylating agents are highly reactive molecules that cause cell death by binding to DNA (Teicher B A. Antitumor alkylating agents. In: DeVita V T Jr, Hellman S, Rosenberg S A, eds. *Cancer: principles and practice of oncology.* 5th ed. Vol. 1. Philadelphia: Lippincott-Raven, 1997:405-18; and Colvin M, Hilton J. Pharmacology of cyclophosphamide and metabolites. Cancer Treat Rep (1981) 65: Suppl 3:89-95). The most frequent site of alkylation in DNA is the $O^6$ position of guanine. Alkylation here forms cross-links between adjacent strands of DNA, R1 which explains how the nitrosoureas, tetrazines, and procarbazine kill cells. The cross-linking of double-stranded DNA by alkylating agents is inhibited by the cellular DNA-repair protein $O^6$-methylguanine-DNA methyltransferase (MGMT). The gene encoding the DNA repair enzyme $O^6$-methylguanine DNA methyltransferase (MGMT) has been found to be inactivated in several human cancers, including a fraction of diffuse large B-cell lymphomas. The MGMT protein (E.C.2.1.1.63), also known as $O^6$-alkylguanine-DNA alkyltransferase (AGT), protects cells from the toxicity of alkylating agents, which frequently target the $O^6$ position of guanine (Ludlum D B. Mutat Res. 1990; 233:117-26; Pegg A E, et al., Prog. Nucleic Acid Res. Mol. Biol. 1995; 51:167-223). The MGMT protein rapidly reverses the formation of adducts at the $O^6$ position of guanine via transfer of the alkyl adduct to a cysteine residue within the protein, thereby averting the formation of lethal cross-links and other mutagenic effects. Thus, the presence of and activity of the enzyme MGMT impedes the activity of chemotherapeutic agents such as alkylating agents. Through this mechanism, MGMT causes resistance to alkylating drugs. Exemplary alkylating agents include carmustine, lomustine, cisplatin, carboplatin, mechlorethamine, cyclophosphamide, ifosfamide, melphalan, chlorambucil, busulfan, thiotepa, dacarbazine, temozolamide or procarbazine.

The level of MGMT varies widely according to the type of tumor, and even varies among tumors of the same type. For example, approximately 30 percent of gliomas lack MGMT (Silber J R, et al., Cancer Res. (1993) 53:3416-3420; Silber J R, et al., Cancer Res. (1998) 58:1068-1073). This deficiency of the enzyme may increase the sensitivity of brain tumors to alkylating agents. Because the MGMT gene is not commonly mutated or deleted, a lack of MGMT may be caused by changes that do not alter the genetic information of the cell.

The invention method includes determining the state of methylation of one or more nucleic acids isolated from the subject. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

The nucleic acid can be any nucleic acid where it is desirable to detect the presence of a differentially methylated CpG island. A CpG island is a CpG rich region of a nucleic acid sequence. The nucleic acid includes, for example, a nucleic acid encoding the enzyme MGMT. The nucleic acid of interest encodes the regulatory region of the enzyme gene as well as the protein coding region.

Any nucleic acid sample, in purified or nonpurified form, can be utilized in accordance with the present invention, provided it contains, or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G•C base pairs. In certain regions, the density of CpG doublets reaches the predicted value; it is increased by ten fold relative to the rest of the genome. CpG islands have an average G•C content of about 60%, compared with the 40% average in bulk DNA. The islands take the form of stretches of DNA typically about one to two kilobases long. There are about 45,000 such islands in the human genome.

In many genes, the CpG islands begin just upstream of a promoter and extend downstream into the transcribed region.

Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the state of methylation of nucleic acids contained in the sample or detection of methylated CpG islands may be extracted by a variety of techniques such as that described by Sambrook, et al. (*Molecular Cloning: A Laboratory Manual*, Cold Spring Harbor, N.Y., 1989; incorporated in its entirety herein by reference).

Many nucleic acid molecules encoding polypeptides and proteins contain a regulatory region which is a region of DNA that encodes information that directs or controls transcription of the nucleic acid. Regulatory regions include at least one promoter. A "promoter" is a minimal sequence sufficient to direct transcription, to render promoter-dependent gene expression controllable for cell-type specific, tissue-specific, or inducible by external signals or agents. Promoters may be located in the 5' or 3' regions of the gene. Promoter regions, in whole or in part, of a number of nucleic acids can be examined for sites of CG-island methylation.

Nucleic acids isolated from a subject are obtained in a biological specimen from the subject. The nucleic acid can be isolated from tumor tissue, brain tissue, cerebrospinal fluid, blood, plasma, serum, lymph, lymph nodes, spleen, liver, bone marrow, or any other biological specimen. Tumor tissue, blood, plasma, serum, lymph, brain tissue, cerebrospinal fluid and bone marrow are obtained by various medical procedures known to those of skill in the art.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not invade surrounding tissues or metastasize to distant sites. The term "malignant" refers to a tumor that is metastastic, invades contiguous tissue or no longer under normal cellular growth control.

A tumor that involves a tissue or organ of the central nervous system is referred to herein as a "brain tumor". A brain tumor can a glioma, an anaplastic astrocytoma, a gliobalstoma multiforme, a low grade astrocytoma glioblastoma, a medulloblastoma, an oligodendroglioma or a neuroblastoma, for example.

A tumor that involves lymphoid cells is referred to herein as a "lymphoma". Lymphomas principally involve the lymph nodes, spleen, liver and bone marrow, although they may infiltrate or spread to any organ or tissue. Malignant lymphomas are clonally derived from the malignant transformation of a single lymphocyte that is arrested at a s specific stage of B- or T-lymphoid cell differentiation. The neoplastic lymphocytes often express the functional and proliferative characteristics of their normal counterparts. For example, the cells of low-grade B-cell lymphomas may also exhibit a follicular pattern. The more mature T-helper cell lymphomas may display hypergammaglobulinemia. Better differentiated B- and T-cell type lymphomas usually retain the migratory and homing characteristics of their normal counterparts. Low grade B-cell lymphomas are, therefor, widespread at the time of diagnosis, and involvement is often initially restricted to the B cell-dependent regions of the lymph nodes and spleen. The cell in the intermediate and high grade lymphomas have a resemblance to normal activated lymphocytes. Once third of diffuse large cell lymphomas are clinically localized disorders at the time of diagnosis, possibly reflecting a loss of normal lymphoid migratory characteristics. One diffuse large cell lymphoma, diffuse large cell B lymphoma, an intermediate grade lymphoma, is the most common lymphoma in the United States (See Bonner, H, et al., The Blood and the Lymphoid Organs, in Pathology, third edition, E Rubin and J L. Farber, eds., Lippincott-Raven, 1999.)

Invention methods are useful for predicting a clinical response to treatment with a chemotherapeutic agent of colorectal tumors, colon tumors, lung tumors, preferably non-small cell lung tumors and head and neck tumors.

As used herein, "a clinical response" is the response of the tumor to treatment with a chemotherapeutic agent. Criteria for determining a response to therapy are widely accepted and enable comparisons of the efficacy alternative treatments (see Slapak and Kufe, Principles of Cancer Therapy, in *Harrisons's Principles of Internal Medicine*, $13^{th}$ edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

With respect to response to treatment of gliomas, a complete response is defined as the absence of any evidence of the tumor on computed tomographic (CT) or magnetic resonance imaging (MRI) scans, for example, with no need for steroid treatment and an improvement in the subject's general condition. Subjects with persistent CT abnormalities but with more than a 50 percent reduction in both the diameter and the volume of the tumor, a reduced need for steroid treatment, and a stabilized neurologic condition are considered to have a partial response. The disease is considered to have progressed if both the diameter and volume of the tumor increased by 25 percent or more of the initial measurements, if a new lesion is evident on CT or MRI scans, or if the subject's neurologic condition worsened and required an increased dose of steroids.

With respect to subjects diagnosed as having a lymphoma, complete remission (CR) is defined as the absence of any detectable disease. Subjects with persistent CT abnormalities, but regression greater than about 75% of initial tumor volume with no signs or symptoms of active disease are considered to be in complete remission if the radiological abnormalities are subsequently stable for at least three months. A partial remission (PR) is defined as an approximately 50% or greater reduction in tumor volume. Failure is defined as anything less than a PR, progressive disease, or treatment related death.

In one aspect of the invention, the state of methylation of the nucleic acid obtained from a subject and encoding an enzyme is hypermethylation as compared with the same region of the nucleic acid in a subject not in need of chemotherapeutic treatment. "Hypermethylation", as used herein, is the presence of methylated alleles in one or more nucleic acids. Nucleic acid encoding a DNA repair enzyme from a subject not in need of chemotherapeutic treatment contains no detectable methylated alleles when the same nucleic acid is examined.

A method for determining the methylation state of nucleic acids is described in U.S. Pat. No. 6,017,704 and U.S. Pat. No. 5,786,146, each of which is incorporated herein in its entirety and described briefly herein. Determining the methylation state of the nucleic acid includes amplifying the nucleic acid by means of oligonucleotide primers that distinguishes between methylated and unmethylated nucleic acids.

Two or more markers can also be multiplexed in a single amplification reaction to generate a low cost, reliable method for predicting a clinical response to treatment with a therapeutic agent. A combination of DNA markers for one ore more CpG-rich regions of one or more nucleic acids may be amplified in a single amplification reaction. The markers are multiplexed in a single amplification reaction, for example, by combining primers for more than one locus. The reaction products are separated on a denaturing polyacrylamide gel, for example, and then exposed to film or stained with ethidium bromide for visualization and analysis. By analyzing a panel of markers, there is a greater probability of producing a more useful methylation profile for a subject.

If the sample is impure (e.g., the sample contains tissues or cells not of interest), it may be treated before amplification with a reagent effective for lysing the cells contained in the fluids, tissues, or animal cell membranes of the sample, and for exposing the nucleic acid(s) contained therein. Methods for purifying or partially purifying nucleic acid from a sample are well known in the art (e.g., Sambrook et al., *Molecular Cloning: A Laboratory Manual*, Cold Spring Harbor Press, 1989, herein incorporated by reference).

Primers hybridize with target polynucleotide sequences. Illustrative oligonucleotide primers specifically targeted to methylated and unmethylated genes encoding MGMT and associated CpG islands include SEQ ID NO:1 to SEQ ID NO:4. SEQ ID NO:1 (5'TTTGTGTTTTGATGTTTGTAG-GTTTTTGT3') and SEQ ID NO:2 (5'AACTCCACACTCT-TCCAAAAACAAAACA3') are forward and reverse primers, respectively, that recognize unmethylated MGMT, and SEQ ID NO:3 (5'TTTCGACGTTCGTAGGTTTTCGC3') and SEQ ID NO:4 (5'GCACTCTTCCGAAAAC-GAAACG3') are forward and reverse primers, respectively, that recognize methylated MGMT.

Detection of differential methylation can be accomplished by contacting a nucleic acid sample with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease that cleaves both methylated and unmethylated CpG-sites, under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified by conventional methods such as PCR wherein primers complementary to the oligonucleotides are employed. Following identification, the methylated CpG-containing nucleic acid can be cloned, using method well known to one of skill in the art (see Sambrook et al., *Molecular Cloning: A Laboratory Manual*, Cold Spring Harbor Press, 1989).

As used herein, a "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of a methylation sensitive restriction endonucleases include SmaI, BssHII, or HpaII, MspI, BSTUI, and NotI. Such enzymes can be used alone or in combination. Other methylation sensitive restriction endonucleases will be known to those of skill in the art and include, but are not limited to SacII, and EagI, for example. An "isoschizomer" of a methylation sensitive restriction endonuclease is a restriction endonuclease which recognizes the same recognition site as a methylation sensitive restriction endonuclease but which cleaves both methylated and unmethylated CGs. One of skill in the art can readily determine appropriate conditions for a restriction endonuclease to cleave a nucleic acid (see Sambrook et al., *Molecular Cloning: A Laboratory Manual*, Cold Spring Harbor Press, 1989).

A nucleic acid of interest is cleaved with a methylation sensitive endonuclease. Cleavage with the methylation sensitive endonuclease creates a sufficient overhang on the nucleic acid of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of sufficient length to allow specific hybridization of an oligonucleotide of interest. Sufficient overhang is at least two bases in length or four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

Cleavage with a methylation sensitive endonuclease results in a reaction product of the nucleic acid of interest that has a blunt end or an insufficient overhang. Blunt ends refers to a flush ending of two stands, the sense stand and the antisense strand, of a nucleic acid. Once a sufficient overhang is created on the nucleic acid of interest, an oligonucleotide is ligated to the nucleic acid cleaved of interest which has been cleaved by the methylation specific restriction endonuclease. "Ligation" is the attachment of two nucleic acid sequences by base pairing of substantially complementary sequences and/or by the formation of covalent bonds between two nucleic acid sequences.

An adaptor can be utilized to create DNA ends of desired sequence and overhang. An "adaptor" is a double-stranded nucleic acid sequence with one end that has a sufficient single-stranded overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. Adaptors can be obtained commercially, or two oligonucleotides can be utilized to form an adaptor. Thus, two oligonucleotides can be used to form an adaptor; these oligonucleotides are substantially complementary over their entire sequence except for the region(s) at the 5' and/or 3' ends that will form a single stranded overhang. The single stranded overhang is complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adaptor under appropriate conditions. The conditions will vary depending on the sequence composition (GC versus AT), the length, and the type of nucleic acid (see Sambrook et al., *Molecular Cloning: A Laboratory Manual*, 2nd Ed.; Cold Spring Harbor Laboratory Press, Plainview, N.Y., 1998).

Following the ligation of the oligonucleotide, the nucleic acid of interest is amplified using a primer complementary to the oligonucleotide. Specifically, the term "primer" as used herein refers to a sequence comprising two or more deoxyribonucleotides or ribonucleotides, preferably more than three, and more preferably more than eight, wherein the sequence is capable of initiating synthesis of a primer extension product, which is substantially complementary to a nucleic acid such as an adaptor or a ligated oligonucleotide. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer can be an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process which is an enzymatic chain reaction that produces exponential quantities of target locus relative to the number of reaction steps involved (e.g., polymerase chain reaction or PCR). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and −strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers used in invention methods may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066, incorporated by reference in its entirety.

Another method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA.

The term "modifies" as used herein means the conversion of an unmethylated cytosine to another nucleotide which will facilitate methods to distinguish the unmethylated from the methylated cytosine. Preferably, the agent modifies unmethylated cytosine to uracil. Preferably, the agent used for modifying unmethylated cytosine is sodium bisulfite, however, other agents that similarly modify unmethylated cytosine, but not methylated cytosine can also be used in the method. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

The primers used in the invention for amplification of the CpG-containing nucleic acid in the specimen, after bisulfite modification, specifically distinguish between untreated or unmodified DNA, methylated, and non-methylated DNA. MSP primers for the non-methylated DNA preferably have a T in the 3' CG pair to distinguish it from the C retained in methylated DNA, and the complement is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Where the nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7-9. Preferably, a molar excess (for genomic nucleic acid, usually about 108:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added is generally be in molar excess over the amount of complementary strand (template) when the sequence to be amplified is contained in a mixture of complicated long-chain nucleic acid strands a large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation such as Taq DNA polymerase, and the like). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487-491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95. degree C.) and incubation at a temperature permitting primer: adaptor hybridization and copying of the master-cut DNA fragment by the amplification enzyme. Heat stable amplification enzymes like *Thermus aquaticus* or *Thermococcus litoralis* DNA polymerases which eliminate the need to add enzyme after each denaturation cycle, are commercially available. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include *Escherichia coli* DNA polymerase I, Klenow fragment of *E. coli* DNA polymerase I, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Q.beta. replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE (Biorad), and NYTRAN. Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Another embodiment of the invention provides a method of treating cancer in a subject with an alkylating chemotherapeutic agent that includes predicting a clinical response to treatment by determining the state of methylation of a nucleic acid isolated from the subject. The nucleic acid encodes an enzyme that impedes an activity of the alkylating chemotherapeutic agent. The state of methylation of the nucleic acid encoding the enzyme is compared to the state of methylation of a nucleic acid encoding the enzyme from a subject not in need of treatment. The state of methylation is indicative of the level of the enzyme.

As used herein, "a subject in need" refers to an individual in need of chemotherapeutic treatment. The subject may be diagnosed as having a disease susceptible to treatment with a chemotherapeutic agent by various methods known to those of skill in the art and include blood tests, x-rays, and biopsy. Such diseases include cellular proliferative disorders including cancers.

Invention methods are ideally suited for the preparation of a kit. Therefore, in accordance with another embodiment of the present invention, there is provided a kit for predicting the response to chemotherapeutic treatment of a cellular proliferative disorder in a subject. Invention kits include a first container containing a reagent which modifies unmethylated cytosine and a second container containing primers for amplification of a CpG-containing nucleic acid, wherein the primers distinguish between modified methylated and nonmethylated nucleic acid. Primers contemplated for use in accordance with the invention include primers having the sequences set forth in SEQ ID NO: 1 to SEQ ID NO:4. The kit further includes primers for the amplification of control nucleic acid. The kit may further include nucleic acid amplification buffer. Preferably, the reagent that modifies unmethylated cytosine is bisulfite.

The kit of the invention is intended to provide the reagents necessary to perform chemical modification and PCR amplification of DNA samples to determine their methylation status. The primer sets included in the kit include a set that anneals to unmethylated DNA that has undergone a chemical modification; a set that anneals to methylated DNA that has undergone a chemical modification; and a primer set that serves as a control for the efficiency of chemical modification. The control primer set should anneal to any DNA (unmethylated or methylated) that has not undergone chemical methylation. In the case of incomplete chemical modification (up to about 50%), data interpretation can still proceed.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing an oligonucleotide for ligation to nucleic acid cleaved by a methylation sensitive restriction endonuclease. One or more container means can also be included comprising a primer complementary to the oligonucleotide. In addition, one or more container means can also be included which comprise a methylation sensitive restriction endonuclease. One or more container means can also be included containing an isoschizomer of said methylation sensitive restriction enzyme.

The above disclosure generally describes the present invention. A more complete understanding can be obtained by reference to the following specific examples provided herein for purposes of illustration only and are not intended to limit the scope of the invention.

EXAMPLE 1

Analysis of Methylation

DNA was extracted according to standard protocols known to those of skill in the art (see, e.g., Sambrook et al., *Molecular Cloning: a Laboratory Manual*, 2nd Ed.; Cold Spring Harbor Laboratory Press, Plainview, N.Y., 1998, herein incorporated by reference). Methylation patterns in the CpG island of MGMT were determined by chemical modification of unmethylated, but not methylated, cytosines to uracil. Methylation-specific polymerase chain reaction (PCR) was performed with primers specific for either methylated or the modified unmethylated DNA, as previously described (Esteller, et al. Cancer Res 1999; 59:793-797; incorporated herein by reference in its entirety; and Herman et al. *Proc Natl Acad Sci U S A* 1996;93:9821-9826; incorporated herein by reference in its entirety). DNA (1 µg) was denatured with sodium hydroxide and modified with sodium bisulfite. DNA samples were then purified with the Wizard DNA purification resin (Promega, Madison, Wis.), again treated with sodium hydroxide, precipitated with ethanol, and resuspended in water. Primer sequences for the unmethylated reaction were 5'TTTGTGTTTTGATGTTTGTAGGTTTTTGT3' (forward primer; SEQ ID NO:1) and 5'AACTCCACACTCTTC-CAAAAACAAAACA3' (reverse primer; SEQ ID NO:2), and for the methylated reaction they were 5'TTTCGACGT-TCGTAGGTTTTCGC3' (forward primer; SEQ ID NO:3) and 5'GCACTCTTCCGAAAACGAAACG3' (reverse primer; SEQ ID NO:4). The annealing temperature was 59° C. Placental DNA treated in vitro with Sss I methyltransferase (New England Biolabs, Beverly, Mass.) was used as a positive control for methylated alleles of MGMT, and DNA from normal lymphocytes was used as a negative control. Controls without DNA were used for each set of methylation-specific PCR assays. Ten microliters of each 50-µl methylation-specific PCR product was loaded directly onto nondenaturing 6 percent polyacrylamide gels, stained with ethidium bromide, and examined under ultraviolet illumination.

EXAMPLE 2

Statistical Analysis

Continuous variables were compared with the use of Student's t-test. Contingency tables were analyzed by Fisher's exact test. Disease-free and overall survival curves were estimated by the Kaplan-Meier method and were compared with the use of the log-rank test. Multivariate survival analyses were performed with the Cox proportional-hazards model, and proportional-hazards assumptions were checked with the use of Schoenfeld residuals and graphic methods. Descriptive or stratified analyses always preceded parametric modeling in order to confirm that the assumptions underlying the models were met. The results are reported as two-sided P values with 95 percent confidence intervals. Analyses were performed with the use of JMP software (version 3.1, SAS Institute, Cary, N.C.) and Stata software (version 6.0, Stata, College Station, Tex.).

EXAMPLE 3

Brain Tumor Subjects and Specimens

Specimens of brain tumors from 47 consecutive subjects referred to the University Hospital of Navarre, in Pamplona, Spain, between April 1993 and November 1998 were studied. All the subjects provided written informed consent. All had histologically verified tumors: Eighteen had an anaplastic astrocytoma, and 29 had a glioblastoma multiforme. Subjects were 38 to 70 years old (median age at diagnosis, 55 years); 30 were men, and 17 were women. Tumor specimens were obtained by resection or biopsy performed before the initiation of treatment with radiation and chemotherapy and were immediately frozen and stored at −80° C. All subjects were treated with intraarterial cisplatin (50 mg per square meter of body-surface area), whole-brain radiotherapy, and a median of three courses of intravenous carmustine (1,3-bis(2-chloroethyl)-1-nitrosourea, or BCNU; 100 mg per square meter) given at four-week intervals. Fifteen of the subjects also underwent autologous bone marrow transplantation plus high-dose chemotherapy treatment with three doses of intravenous carmustine (300 mg per square meter) per day and one dose of intraarterial cisplatin (100 mg)

The response to treatment was evaluated after the subjects had completed therapy. A complete response was defined as the absence of any evidence of the tumor on computed tomographic (CT) and magnetic resonance imaging (MRI) scans, with no need for steroid treatment and an improvement in the subject's general condition. Subjects with persistent CT abnormalities but with more than a 50 percent reduction in both the diameter and the volume of the tumor, a reduced need for steroid treatment, and a stabilized neurologic condition were considered to have a partial response. The disease was considered to have progressed if both the diameter and volume of the tumor increased by 25 percent or more of the initial measurements, if a new lesion was evident on CT or MRI scans, or if the subject's neurologic condition worsened and required an increased dose of steroids.

EXAMPLE 4

Predicting Clinical Responses of Gliomas

Forty-seven newly diagnosed grade III or IV gliomas (classified as anaplastic astrocytoma in 18 subjects and as glioblastoma multiforme in 29) were analyzed. The characteristics of the subjects are shown in Table 1. Methylation of the MGMT promoter was found in 19 of the 47 tumors (40 percent) a frequency similar to that found in a previous study (Estellar, 1999, supra) and consistent with that in other reports (Silber et al., Cancer Res 1993; 53:3416-3420; and Silber et al., Cancer Res 1998; 58:1068-1073). Methylation was not associated with the subject's age, the Karnofsky score for performance status, or the grade of the tumor (P>0.3 for each comparison).

TABLE 1

| CHARACTERISTIC | UNMETHYLATED (N = 28) | METHYLATED (n = 19) |
|---|---|---|
| | number of subjects (%) | |
| Age | | |
| ≦50 years | 8 (29) | 8 (42) |
| >50 years | 20 (71) | 11 (58) |
| Sex | | |
| Male | 14 (50) | 16 (84) |
| Female | 14 (50) | 3 (16) |
| Karnofsky score | | |
| ≦80 | 18 (64) | 13 (68) |
| >80 | 10 (36) | 6 (32) |
| Type of tumor | | |
| Anaplastic astrocytoma | 11 (39) | 7 (37) |
| Glioblastoma multiforme | 17 (61) | 12 (63) |

Figure 3A:
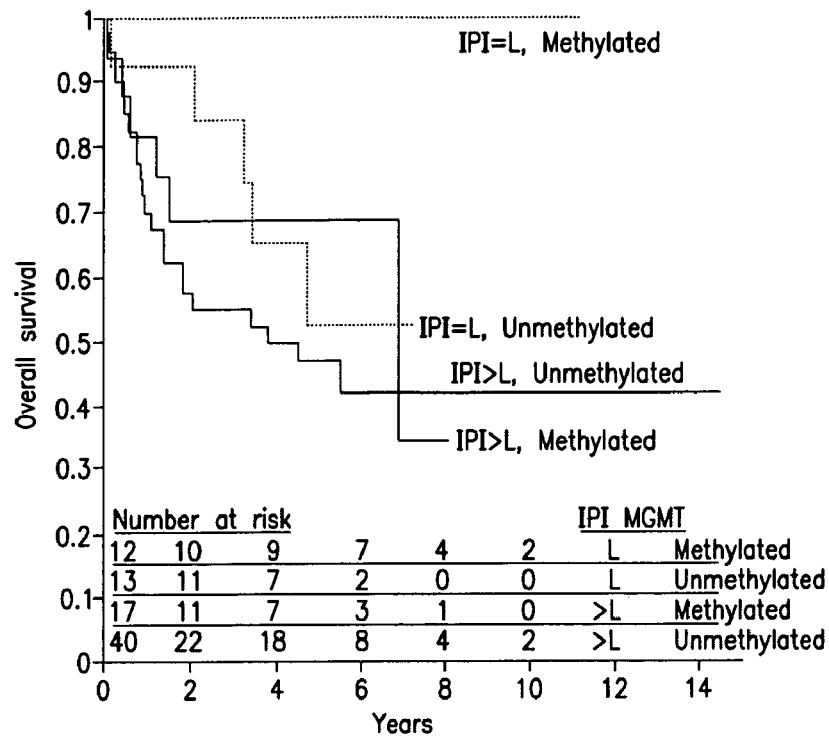
FIG. 3A shows overall survival as a function of MGMT methylation status and IPI.
Figure 3B:
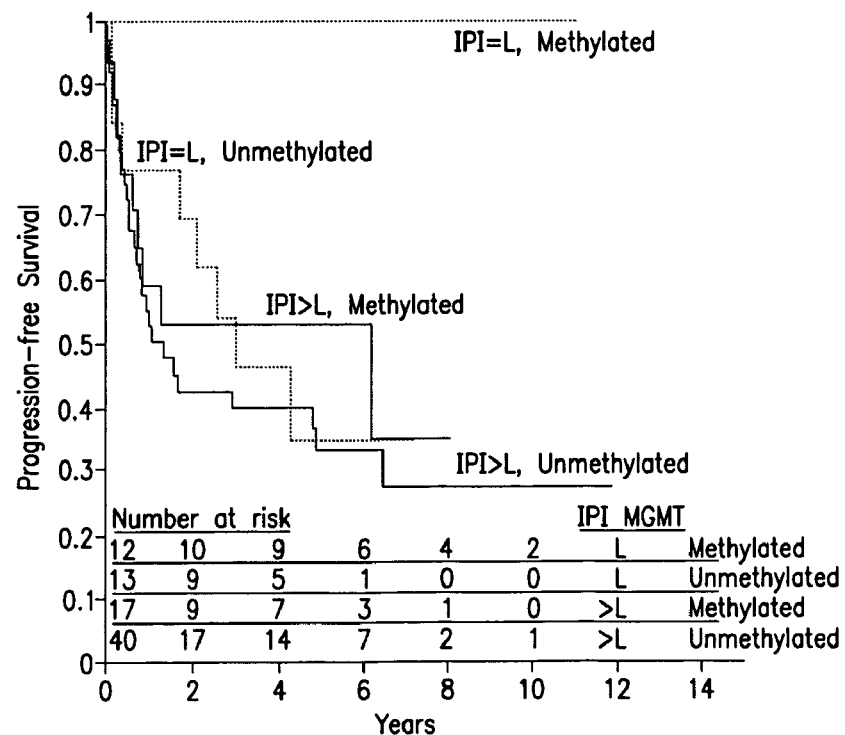
FIG. 3B shows failure-free survival as a function of MGMT methylation status and IPI. Statistical analysis examined IPI as a continuous variable.

In univariate analyses, methylation of the promoter was positively correlated with the clinical response and with overall and disease-free survival. Twelve of the 19 subjects with methylated tumors (63 percent) had a partial or complete response to carmustine, as compared with one of the 28 subjects with unmethylated tumors (4 percent, P<0.001) (Table 2). The lack of methylation was associated with a much higher risk of death (hazard ratio, 9.5; 95 percent confidence interval, 3.0 to 42.7; P<0.001) (FIG. 3A). In univariate analysis, no other factor had a statistically significant relation with survival. The median time to the progression of disease was 21 months for methylated gliomas and 8 months for unmethylated gliomas (P<0.001), and the hazard ratio associated with nonmethylation was 10.8 (95 percent confidence interval, 4.4 to 30.8) (FIG. 3B). The small number of deaths among subjects with gliomas containing a methylated promoter (four deaths) made multivariate analyses unreliable. The hazard ratio associated with a nonmethylated glioma was either unchanged or increased when other predictors were added individually to the model.

TABLE 2

| RESPONSE | UNMETHYLATED (N = 28) | | METHYLATED (N = 19) | |
|---|---|---|---|---|
| | no. | % (95% CI) | no. | % (95% CI) |
| Complete | 0 | 0 (0-12) | 2 | 11 (1-33) |
| Partial | 1 | 4 (0-18) | 10 | 52 (29-76) |
| No Change | 4 | 14 (4-33) | 3 | 16 (3-38) |
| Progression | 23 | 82 (63-94) | 4 | 21 (6-44) |

CI* denotes confidence interval

It has been reported that lack of MGMT in gliomas from subjects who were treated with chloroethylnitrosoureas had only a moderate effect on overall survival, and the time to progression of disease was affected minimally or not at all (Belanich et al. Cancer Res. 1996; 56:783-788; Jaeckle et al. J. Clin. Oncol. 1998; 16:3310-3315; and Silber et al. Clin. Cancer Res. 1999; 5:807-814). Using a different method to evaluate the status of the MGMT gene, the study described herein found a much stronger influence of the presence or absence of the enzyme. The accumulation of normal cells in the tumor, including infiltrating lymphocytes, may complicate accurate assessment of MGMT. The mixture of normal cells may explain, in part, the difference between the biochemical activity measured in tumor homogenates9 and the results of direct immunohistochemical examination of MGMT in tumor cells. The use of methylation-specific PCR permits an assessment of methylation of the MGMT promoter. Methylation status is an indicator of the transcriptional activity of the gene in glioma cells, and thus the presence or absence of the DNA-repair enzyme.

In the study described herein, methylation of the MGMT promoter was associated with responsiveness to carmustine and an increase in overall survival and the time to progression of disease. Moreover, the methylation status of the promoter was more predictive of the outcome of carmustine treatment than the grade of the tumor, the Karnofsky performance status, or the subject's age. Because methylation of the MGMT promoter can predict responsiveness to carmustine, the use of this alkylating agent might be reserved for subjects with gliomas in which the promoter is methylated. Moreover, it might be possible to increase the sensitivity of resistant tumors (those without methylation) with the use of agents that inhibit the MGMT enzyme. One such inhibitor, $O^6$-benzylguanine, is being investigated for this purpose. It is a substrate for MGMT that inactivates the enzyme. $O^6$-benzylguanine has been shown to enhance the response to alkyl nitrosoureas in vitro and in vivo (Dolan and Pegg, Clin. Cancer Res. 1997; 3:837-847 and Dolan et al. Proc. Natl. Acad. Sci. U S A 1990; 87:5368-5372). The use of such an agent to increase the sensitivity of gliomas to carmustine only in cases of resistant tumors might prevent the toxic effects of the combination of these drugs on normal tissues in subjects who are already sensitive to carmustine.

EXAMPLE 5

Lymphoma Subject Population and Specimen Procurement

Eighty-four subjects with previously untreated diffuse large B-cell lymphoma (B-DLCL), who had been consecutively diagnosed and treated at three Italian institutions from 1986 to 1997 and whose DNA was available were used for this study. Clinical follow-up was obtained until 31 Aug. 1999 or until death. The median follow-up duration from initiation of treatment for censored subjects was 61 months. Diagnosis was based on histopathology, immunophenotypic analysis of cell surface markers, and immunogenotypic analysis of immunoglobulin gene rearrangement. The histopathologic definition of B-DLCL was according to the REAL classification (Harris N L, et al., Blood. 1994;84:1361-92). Subjects positive for human immunodeficiency virus were not included in the study. Staging included routine blood chemistry tests; blood cell counts and differential; EKG; chest x-ray; computed tomography of chest, abdomen and pelvis; and bilateral bone marrow biopsy in all subjects. Disease stage was assessed according to Ann Arbor criteria (Carbone P P, et al., Cancer Res. 1971;31:1860-1). The International Prognostic Indicator (IPI) was calculated as described (The International Non-Hodgkin's Lymphoma Prognostic Factors Project. A predictive model for aggressive non-Hodgkin's lymphoma. N Engl J Med. 1993;329:987-94), with subjects classified as Low, Low-Intermediate, High-Intermediate, and High risk.

Treatment varied, depending on stage of disease, date of diagnosis, institution and prognostic factors. However, all subjects were treated with cyclophosphamide and an anthracycline containing regimen. Nine subjects with localized stage of disease without adverse prognostic features were treated with a brief chemotherapy, ACOPB (Adriamycin, Cyclophosphamide, Vincristine, Prednisone, Bleomycin) or three courses of CHOP (Cyclophosphamide, Adriamycin, Vincristine, Prednisone), followed by locoregional radiotherapy at a dose of 36 Gy. Forty-two subjects with localized stage and adverse prognostic features or advanced stage disease were treated with CHOP (29 subjects) or a third generation chemotherapy scheme such as MACOPB (Methotrexate, Adriamycin, Cyclophosphamide, Vincristine, Prednisone, Bleomycin) (6 subjects) or VACOPB (Etoposide, Adriamycin, Cyclophosphamide, Vincristine, Prednisone, Bleomycin) (7 subjects). Fifteen elderly subjects, over 65 years, received PVEBEC (Prednisone, Vinblastine, Epirubicin, Bleomycin, Etoposide, Cyclophosphamide). Eighteen subjects, with advanced stage and adverse prognostic features were treated with a reduced course of standard chemotherapy (MACOPB or CHOP) followed by an intensification chemotherapy with peripheral blood stem cell harvest and high dose chemotherapy BEAM (Carmustine, Etoposide, ARA-C, Melphalan) with autologous stem cell transplantation.

Response to treatment was evaluated after the completion of the therapeutic program. Re-staging tests included blood chemistries and CT scans of chest, abdomen and pelvis in all subjects and repetition of bone marrow biopsy if abnormal at diagnosis. Complete remission (CR) was defined as the absence of any detectable disease. Subjects with persistent CT abnormalities, but regression greater than 75% of initial tumor volume with no signs or symptoms of active disease were considered to be in complete remission if the radiological abnormalities were subsequently stable for at least three months. A partial remission (PR) was defined as a 50% or greater reduction in tumor volume. Failure was defined as anything less than a PR, progressive disease, or treatment related death.

EXAMPLE 6

Analysis of MGMT Expression in Lymphomas by Immunohistochemistry

The correlation between MGMT methylation status and MGMT protein expression was assessed in a representative panel of 26 lymphomas. Sections of formalin-fixed, paraffin-embedded tissue sections were deparaffinized with xylene for 30 seconds and dehydrated by using graded ethanols and treated for 30 minutes in TEC (Tris-EDTA-Citrate) solution (pH 7.8) in microwave oven at 250W. Immunohistochemistry was performed using the ABC method (ABC-Elite kit, Vector, Burlingame, Calif.). Immunoperoxidase staining using diaminobenzidine as chromogen was performed on an automated immunostainer (Ventana Medical Systems, Inc, Tucson, Ariz.) according to the company's protocols. Commercially available mouse anti-MGMT monoclonal antibody (clone MT3.1; Chemicon Intl., Temecula, Calif.) at 1:100 was used (Brent T P, et al. Cancer Res. 1990;50:58-61). The antibody has previously been demonstrated to be useful for immunohistochemistry and to correlate with MGMT activity (Reese J S, et al., Proc Natl Acad Sci USA. 1996;93:14088-93). Nuclear staining was determined by two authors (A. G. and A. C.) who did not have knowledge of the molecular analysis of the samples.

EXAMPLE 7

MGMT promoter hypermethylation was examined in 84 subjects with B-DLCL (clinical description of this population in Table 3). MGMT hypermethylation was found in 30 of 84 (36%) B-DLCL. As in the study of brain tumor subjects, MGMT hypermethylation correlated with absent MGMT protein expression, since all (n=17) lymphoma samples carrying MGMT hypermethylation failed to express the protein as tested by immunohistochemistry. Conversely, all (n=9) lymphoma samples carrying unmethylated MGMT alleles expressed the MGMT protein as tested by immunohistochemistry.

The presence of MGMT methylation was not associated with any difference in clinical stage, performance status or LDH levels (see Table 3, all p-values>0.15). Subjects with MGMT methylation experienced 77% CR, 13% PR, and 10% NR (N=30), versus 63% CR, 15% PR and 22% NR (N=54) among those without methylation. This trend for improved response in subjects with tumors containing MGMT methylation was not statistically significant (p=0.3) but is consistent with an increased sensitivity of lymphomas with MGMT methylation.

TABLE 3

|  | UNMETHYLATED (n = 54) | | METHYLATED (n = 30) | |
| --- | --- | --- | --- | --- |
|  | No. | % | No. | % |
| Stage | | | | |
| I-II | 15 | 28 | 11 | 37 |
| III-IV | 39 | 72 | 19 | 63 |
| Performance Status | | | | |
| 0-1 | 35 | 65 | 22 | 73 |
| 2-3 | 19 | 35 | 8 | 27 |
| LDH | | | | |
| ≦450 U/l | 22 | 41 | 14 | 47 |
| >450 U/l | 26 | 48 | 13 | 43 |
| Not Available | 6 | 11 | 3 | 10 |

Figure 2B:
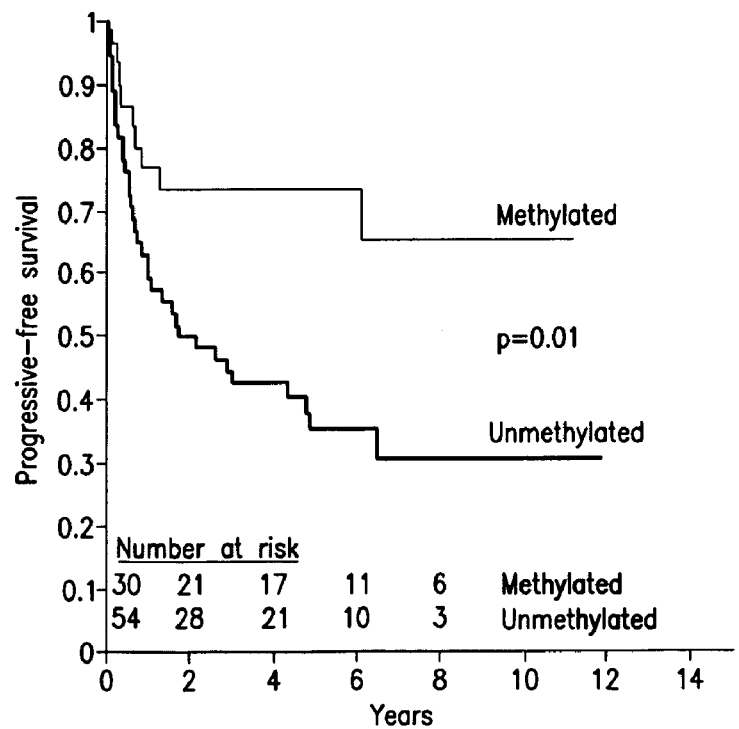
FIG. 2B shows failure-free survival as a function of MGMT methylation status. In AA and AB significantly increased survival was noted in subjects with aberrant MGMT methylation, and this significance was independent of stage, performance status and LDH levels.

However, as was observed for subjects with high-grade gliomas, MGMT methylation status in these lymphoma subjects correlated strongly with overall and progression free survival. Overall survival was significantly increased among lymphoma subjects having MGMT methylation, with the hazard ratio for non-methylation for the outcome of time to death was 2.8 (95% CI, 1.2 to 7.5, p=0.01) (FIG. 2A). Similarly, the hazard ratio for disease progression among those without methylation versus with methylation was 2.6 (95% CI, 1.3 to 5.8, p=0.005, FIG. 2B).

The traditional markers of prognosis in non-Hodgkin's lymphoma which form the International Lymphoma Study Group classification, that is performance status, LDH and disease stage, had weak or modest univariate associations with survival. In contrast, in multivariate survival models, MGMT methylation status was consistently the most important predictor, and only disease stage was statistically significant. In a model where stage was dichotomized (stages 1 and 2 versus 3 and 4), the hazard ratio outcome for time to death for the higher stages was 2.4 (CI, 1.1 to 6.6, p=0.03), and that for non-methylation was virtually identical to the univariate result (HR=2.7, CI 1.2 to 7.2 p=0.02). Similar results were obtained for time to progression for stage (HR=2.5, CI 1.2 to 5.8, p=0.01) and non-methylation status (HR=2.5, CI 1.2 to 5.5, p=0.01).

The International Prognostic Index (IPI) incorporates these individual factors (age, stage, bone marrow involvement, LDH and performance status) into a useful prognostic indicator. To determine whether MGMT methylation was still predictive of survival, MGMT was examined in relation to IPI. As previously demonstrated (The International Non-Hodgkins Lymphoma Prognostic Factors Project. A predictive model for aggressive non-Hodgkin's lymphoma, N. Engl. J. Med., 1999; 329:987-94), the IPI was predictive of time to death with a hazard ratio of 1.6 (CI 1.1 to 2.3, p=0.009) when IPI was coded as a continuous variable. MGMT remained predictive of overall survival in this multivariate analysis (HR=2.3, CI 1.0-6.2, p=0.05). For time to progression, the IPI as a continuous variable was also prognostically important (HR=1.4, CI 1.0-2.0, p=0.02), but MGMT methylation remained an independent predictor of time to progression (HR 2.2, CI 1.06-4.9, p=0.03) in this multivariate analysis.

Several hypotheses may explain the prognostic role of MGMT in predicting B-DLCL survival. A first hypothesis concerns the possibility that MGMT hypermethylation is a prognostic marker of natural history that identifies a specific pathogenetic subset of lymphomas with a more favorable outcome. While it is impossible to completely exclude this explanation, it appears to be independent of other reported prognostic markers. A priori, one would not expect MGMT methylation to be a positive prognostic indicator, but perhaps a negative one, since MGMT hypermethylation has been associated with the formation of k-RAS and p53 mutations (Esteller M, et al. Cancer Res. 2001;61:4689-92) both of which are often negative prognostic markers. The prognostic role of MGMT hypermethylation cannot be ascribed to a clinical advantage of B-DLCL displaying a generalized methylated phenotype, since promoter hypermethylation of other genes frequently methylated in B-DLCL (Katzenellenbogen R A, et al., Blood 1999; 93:4347-4353), namely the death-associated protein kinase gene, does not correlate with outcome (our unpublished observation).

An alternative hypothesis to explain the prognostic importance of MGMT hypermethylation is that MGMT inactivation may render B-DLCL cells more prone to the genotoxic effects of alkylating agents, as it has been recently proposed in the case of glioma (Esteller M, et al., N Engi J. Med. 2000; 343:1350-4). In fact, the DNA repair protein MGMT is one of the key factors mediating resistance to these agents and several reports suggest that MGMT does play a role in modulating cyclophosphamide activity at least in vitro, as demonstrated in lung cancer (Mattern J, et al., Int J Cancer. 1998; 77:919-22), medulloblastoma (Friedman H S, et al. Cancer Chemother Pharmacol. 1999; 43:80-5) and ovarian (CHO) cell lines (Cai Y, et al., Cancer Res. 1999; 59:3059-63). Thus, although MGMT has long been implicated in resistance to methylating and chloroethylating agents, it may also contribute to resistance to the cytotoxic and mutagenic effects of cyclophosphamide (Gamcsik M P, et al., Curr Pharm Des. 1999; 5:587-605). It appears that MGMT activity is important in protecting against the toxicity of acrolein, one of the metabolites of cyclophosphamide, while the toxicity from the other metabolite, phosphoramide mustard, is not repaired by MGMT. Increased sensitivity to alkylating agents conferred by MGMT inactivation may result in complete elimination of all transformed cells, which would otherwise lead to disease recurrence. The absence of statistical difference in initial response of B-DLCL with and without MGMT hypermethylation is at variance with the behaviour of glioma subjects, and may be due to the presence of other potent and effective anticancer agents used as standard treatments for B-DLCL, such as adriamycin, vincristine and etoposide, that might have masked greater differences in response between methylated and unmethylated groups.

Despite these observations, the improved survival in B-DLCL subjects with MGMT hypermethylation cannot be unequivocally attributed to sensitivity to cyclophosphamide. Such a conclusion would only be possible if this agent was used alone and then, only if a non-treatment control was examined. This treatment strategy, however, is not appropriate given the effectiveness of multi-drug regimens for B-DLCL. A putative indirect approach to address the relationship between MGMT status and B-DLCL sensitivity to cyclophosphamide may be the use of the MGMT inhibitor $O^6$-benzylguanine ($O^6$-BG) (Dolan M E, and Pegg A E. Clin Cancer Res. 1997;3:837-47). $O^6$-BG is an MGMT substrate that, by its binding to the protein in a suicide reaction, inactivates MGMT. While this inhibitor has been used primarily to enhance the response to alkyl-nitrosoureas both in vitro and in vivo (Dolan M E, et al., Proc Natl Acad Sci U S A. 1990; 87:5368-72), $O^6$-BG has been shown to increase sensitivity to cyclophosphamide metabolites as well (Cai Y, et al., Cancer Res. 2001; 60:5464-9). The safety profile of $O^6$-BG has allowed its use in phase I clinical trials (Schilsky R L, et al., Clin Cancer Res. 2000; 6:3025-31). The results described herein prompt pre-clinical studies in animal models aimed at defining whether $O^6$-BG has a role in the treatment of B-DLCL carrying unmethylated MGMT genes.

The studies described herein demonstrate that MGMT promoter hypermethylation provides a novel independent marker for the prognostic assessment of B-DLCL survival. MGMT promoter hypermethylation also correlates with an improved clinical response and an increase in overall survival and disease free survival in subjects with glioma tumors treated with BCNU. Assessment of promoter hypermethylation, rather than enzyme activity, may be a more accurate strategy to assess MGMT status in human cancer. In fact, the presence of normal cells, including normal infiltrating lymphocytes, may make determination of MGMT activity within the tumor itself difficult. The PCR approach described herein eliminates the problems of infiltrating normal cells, and thereby may more accurately separate tumors into those with and without MGMT inactivation. Since hypermethylation of MGMT correlates with loss of mRNA expression and appears to be the only mechanism associated with loss of MGMT activity (Qian X C, et al. Cancer Res. 1997; 57:3672-7; Watts G S, et al. Mol Cell Biol. 1997; 17:5612-9; Danam et al. Mol Carcinog. 1999; 24:85-9; and Esteller M. et al., Cancer Res. 2000; 60:2368-71), one can study MGMT loss of function by assessing promoter hypermethylation. This approach examines the lesion itself (epigenetic inactivation of the promoter) rather than the effect of this alteration (loss of protein expression and enzyme activity).

Although the invention has been described with reference to the presently preferred embodiments, it should be understood that various modifications can be made without departing from the spirit of the invention. Accordingly, the invention is limited only by the following claims.

What is claimed is:

1. A method for predicting a clinical response to treatment with an alkylating chemotherapeutic agent of a human subject in need thereof, wherein clinical response is measured by tumor regression, disease-free survival, or survival, comprising:

obtaining a nucleic acid from a brain tumor or a diffuse large B-cell lymphoma of the subject to be treated;

treating the nucleic acid sample with bisulfite to modify unmethylated cytosine residues in the nucleic acid sample;

determining the state of methylation of the promoter of the $O^6$-methylguanine-DNA methyltransferase (MGMT) gene in the nucleic acid sample by amplification with unmethylated-specific primers set forth in SEQ ID NO: 1 and SEQ ID NO: 2, and methylated specific primers set forth in SEQ ID NO: 3 and SEQ ID NO: 4;

comparing the state of methylation with the state of MGMT promoter methylation from an unmethylated control sample;

and predicting the clinical response of the subject in need of treatment based on the comparison, wherein hypermethylation of the MGMT promoter of the subject in need of treatment, as compared with the state of MGMT promoter methylation from an unmethylated control sample, is indicative of increased tumor regression, increased disease-free survival, and increased survival, in response to treatment with an alkylating chemotherapeutic agent.

2. The method of claim 1, wherein the brain tumor is a glioma, an anaplastic astrocytoma, a glioblastoma multiforme, a low grade astrocytoma glioblastoma, a medulloblastoma, an oligodendroglioma or a neuroblastoma.

3. The method of claim 1, wherein the alkylating agent is carmustine, lomustine, cisplatin, carboplatin, mechlorethamine, cyclophosphamide, ifosfamide, melphalan, chlorambucil, busulfan, thiotepa, dacarbazine, temozolamide or procarbazine.

4. The method of claim 1, further comprising hybridizing the methylation specific amplification product to an oligonucleotide probe.

5. The method of claim 4, wherein the oligonucleotide probe comprises a detectable label.

6. The method of claim 5, wherein the detectable label comprises a radioisotope, a fluorescent compound, a bioluminescent compound, a chemiluminescent compound, a metal chelator, or an enzyme.

7. The method of claim 5, wherein the detectable label comprises a fluorescent compound.

* * * * *

UNITED STATES PATENT AND TRADEMARK OFFICE
CERTIFICATE OF CORRECTION

| | | |
|---|---|---|
| PATENT NO. | : 7,655,444 B2 | Page 1 of 1 |
| APPLICATION NO. | : 10/870577 | |
| DATED | : February 2, 2010 | |
| INVENTOR(S) | : Herman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Signed and Sealed this

Twenty-third Day of November, 2010

David J. Kappos
*Director of the United States Patent and Trademark Office*